(12) United States Patent
Bock

(10) Patent No.: US 7,849,548 B2
(45) Date of Patent: Dec. 14, 2010

(54) EXTENDED REACH ULTRASONIC TOOTHBRUSH

(76) Inventor: Robert T. Bock, 66 Drovers La., Brewster, NY (US) 10509

( * ) Notice: Subject to any disclaimer, the term of this patent is extended or adjusted under 35 U.S.C. 154(b) by 418 days.

(21) Appl. No.: 12/072,228

(22) Filed: Feb. 25, 2008

(65) Prior Publication Data
US 2009/0211041 A1    Aug. 27, 2009

(51) Int. Cl.
*A61C 17/20* (2006.01)
*A61C 17/22* (2006.01)
(52) U.S. Cl. .................. 15/22.1; 15/176.1; 433/119
(58) Field of Classification Search .............. 15/22.1, 15/176.1; 433/118, 119
See application file for complete search history.

(56) References Cited

U.S. PATENT DOCUMENTS

| | | | |
|---|---|---|---|
| 3,335,443 A | 8/1967 | Parisi | |
| 3,809,977 A | 5/1974 | Balamuth | |
| 4,192,035 A | 3/1980 | Kuris | |
| 5,138,733 A | 8/1992 | Bock | |
| 5,247,716 A | 9/1993 | Bock | |
| 5,305,492 A | 4/1994 | Giuliani | |
| 5,369,831 A | 12/1994 | Bock | |
| 5,378,153 A | 1/1995 | Giuliani | |
| 7,269,873 B2 | 9/2007 | Brewer | |
| 2005/0049155 A1* | 3/2005 | Gavney et al. | 510/108 |
| 2005/0050659 A1* | 3/2005 | Chan et al. | 15/22.1 |
| 2005/0091770 A1* | 5/2005 | Mourad et al. | 15/22.1 |
| 2005/0283928 A1* | 12/2005 | Grez et al. | 15/22.1 |

FOREIGN PATENT DOCUMENTS

| | | | |
|---|---|---|---|
| JP | 10-165228 | * | 6/1998 |
| JP | 2003-61985 | * | 3/2003 |
| JP | 2003-88426 | * | 3/2003 |
| JP | 2004-57534 | * | 2/2004 |
| JP | 2004-148079 | * | 5/2004 |
| JP | 2005-66024 | * | 3/2005 |
| JP | 2005-80802 | * | 3/2005 |
| JP | 2006-6570 | * | 1/2006 |
| JP | 2006-42991 | * | 2/2006 |
| JP | 2006-312032 | * | 11/2006 |

* cited by examiner

*Primary Examiner*—Mark Spisich

(57) ABSTRACT

An ultrasonic toothbrush for daily oral hygiene application is disclosed, having an ultrasound transducer in direct contact with the fluids in the oral cavity, without ultrasound energy attenuation between the transducer and the fluids in the oral cavity. Maximum level of ultrasound energy coupled to the fluids within the oral cavity and to the teeth and gums and periodontal pockets, achieving maximum loosening of soft plaque. Toothbrush configurations of ultrasonically enhanced manually operated toothbrushes and motorized toothbrushes having lateral direction sonic frequency vibrating brush heads emitting ultrasonic energy are disclosed. To generate the sonic frequency lateral vibration of the brush head, a motion transducer is utilized. Removable and user replaceable brush heads are described. In the various configurations low voltage DC energy supplied by a battery is converted to ultrasonic frequency DC current to activate the ultrasonic transducer. All configurations are utilizing bristle tufts to effectively dislodge plaque loosened by the ultrasonic waves from the surfaces of teeth and gums.

1 Claim, 3 Drawing Sheets

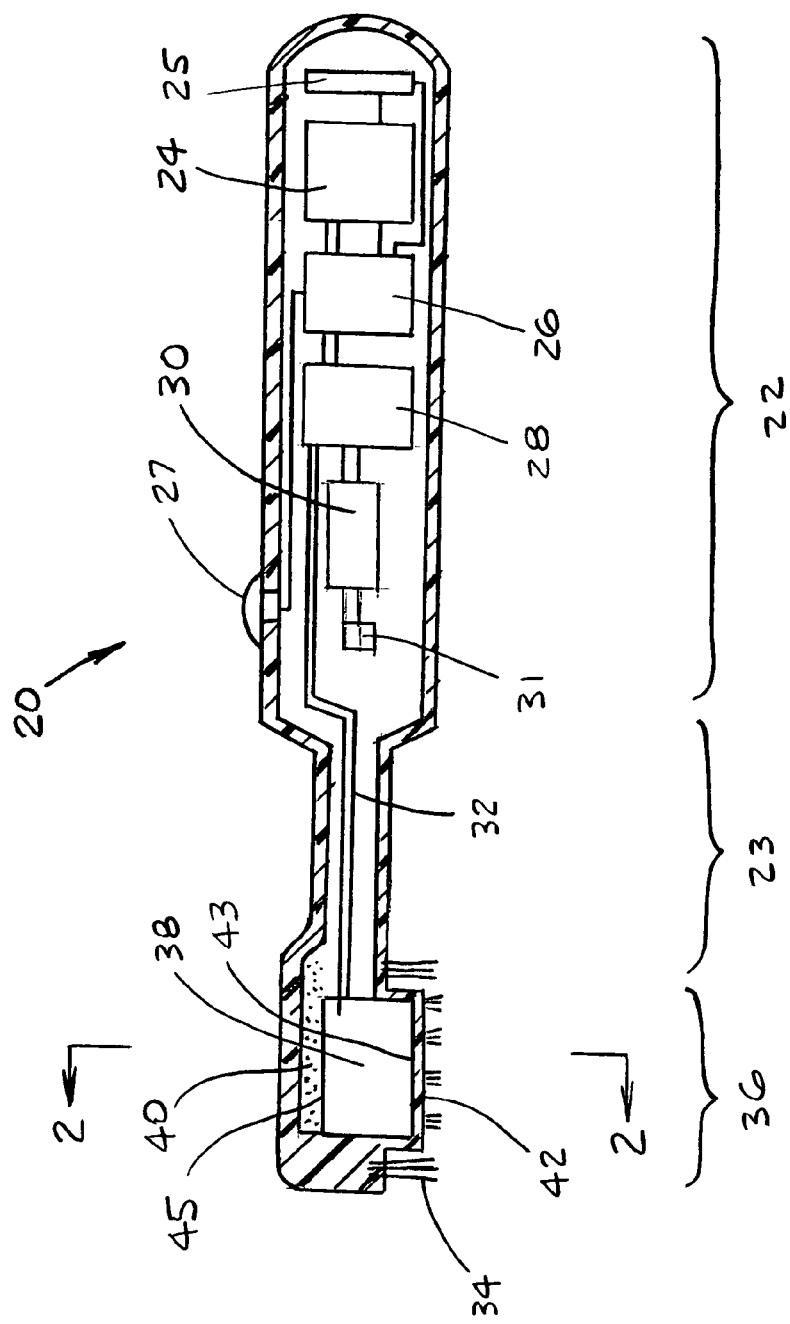
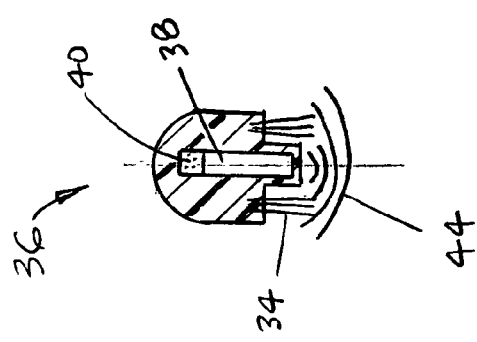

EXTENDED REACH ULTRASONIC TOOTHBRUSH

BACKGROUND

1. Field of Invention

This invention relates to ultrasonic toothbrushes. More particularly the invention is concerned with improving the efficiency of earlier generation ultrasonic toothbrushes, improving the coupling of the ultrasonic energy to the fluids in the oral cavity, and the teeth and gums of the user.

2. Description of Prior Art

Powered toothbrushes introduced in the 1950 period provided an improvement over manual toothbrushes, particularly so for individuals with limited dexterity.

Numerous unsuccessful attempts were made and disclosed by U.S. Pat. No. 3,335,443 by Parisi, U.S. Pat. No. 3,809,977 by Balamuth et. al., U.S. Pat. No. 4,192,035 by Kuris, and others to develop improved powered toothbrushes by attempting to vibrate the brush head or the bristles by ultrasonic means. None of these attempts utilized ultrasound transducers, they have merely proposed to replace the conventional motorized toothbrushes with a higher speed vibration. They had no effort to generate and couple ultrasonic waves to the teeth and gums.

The state of the art remained unchallenged in the marketplace until the introduction of the first commercially available ultrasonic toothbrush in 1992 based on U.S. Pat. No. 5,138,733 by Bock. Advances followed quickly by U.S. Pat. Nos. 5,369,831 and 5,247,716 also by Bock.

In the Bock patents ultrasound is generated by a piezo electric transducer in the tip of the brush and it is conducted to the teeth and gums of the user through three layers of plastic materials, the tip of the toothbrush handle, the brush head, and the bristles. Consequently, some of the ultrasound energy emitted by the transducer is attenuated by the multiple surface interfaces and plastics between the transducer and the oral cavity.

The art was also enhanced in 1992 by U.S. Pat. Nos. 5,305,492 and 5,378,153 both by Giuliani et. al. These patents basically teach a mechanically vibrating brush head in the sonic frequency range of approximately 250 Hertz. The sonic frequency vibration is generated by a pair of electromagnets vibrating a steel resonator arm, which is pivoted around a torsion pin to provide a lateral vibration to the brush head. The physical vibration of the bristles enhances plaque removal and provides a pleasant feeling and instant feedback to the user, but still does not generate or transmit ultrasonic energy to the teeth and gums.

The next improvement of the state of the art is represented by U.S. Pat. No. 7,269,873 B2 by Brewer et. al., entitled "Ultrasonic Toothbrushes employing an Acoustic Waveguide. U.S. Pat. No. 7,269,873 is essentially a modification of U.S. Pat. No. 5,138,733 by Bock. Brewer provides an improvement in the efficiency of the transmission of the ultrasonic waves from the transducer to the oral cavity by the addition of a waveguide, which is more efficient than the bristles described in U.S. Pat. No. 5,138,733 by Bock. However, the waveguide suggested by Brewer, while provides certain advantages, still attenuates the ultrasonic energy produced by the transducer. U.S. Pat. No. 7,269,873 by Brewer still only discloses an invention wherein the surface interface between the ultrasonic transducer and the waveguide still creates attenuation of ultrasound and the long acoustic waveguide material extending from the ultrasound transducer located within the toothbrush body to the tips of the bristles also significantly attenuates the ultrasound energy from the transducer. Due to these two attenuating mechanisms the ultrasonic waves emitted by the transducer are reduced in efficiency and still does not provide the ultimate performance. In addition, the mechanism of U.S. Pat. No. 7,269,873 became much more complex and more expensive than the one invented by Bock in U.S. Pat. No. 5,138,733.

What has occurred to date is that not withstanding the teachings of the prior art, the ability to provide ultrasonic wave transmission effectively, inexpensively, and easily has remained unsolved.

OBJECTS AND ADVANTAGES OF THE INVENTION

Responding to the above-described unresolved needs, this invention provides a highly efficient ultrasonic toothbrush, wherein the attenuation of the ultrasonic waves between the transducer and the oral cavity is minimized, extending the reach of the ultrasonic waves by providing the highest possible level of ultrasonic output from the brush head.

The ultrasonic toothbrush typically comprises a handle portion and a head portion. The handle portion houses a rechargeable battery, an electric motor to generate sonic frequency physical vibration of the head portion through a motion transducer, and an electronic system to provide operational control of the toothbrush. The electronic system typically has an on-off switch, battery charge control, speed control for the motor and generates the ultrasonic frequency electrical current to power the ultrasonic transducer. The head portion of the toothbrush houses the bristle tufts and an ultrasonic transducer, which protrudes from the head portion of the toothbrush.

The protruding and exposed ultrasonic transducer positioned in close proximity to the tips of bristle tufts is the key inventive step in this generation of the ultrasonic toothbrush design. The invention eliminates all of the attenuating surface interfaces of the previous state of art of U.S. Pat. Nos. 5,138,733 and 5,247,716 namely the transducer to the inside surface of the housing, the outside surface of the housing to the inside surface of the brush head, and the brush head to bristle interface. Not using the bristles as the ultrasound transmitting media eliminates the attenuation of the ultrasound by the bristles. The invention is also superior to the acoustic waveguide design shown in U.S. Pat. No. 7,269,873 B2, as explained in the prior art section of the specifications. The current invention eliminates all attenuation of ultrasound energy by placing the ultrasound transducer in direct contact with the mixture of the saliva and the dentifrice in close proximity with the tips of the bristles, wherein this non-attenuated ultrasound energy in combination with the optionally vibrating bristle tufts create mild cavitation and acoustic streaming within the fluids in the oral cavity, enhancing the plaque removing action of the bristles. The invention eliminates the attenuation of the ultrasound energy emitted by the piezoelectric transducer by eliminating all surface interfaces, bristles, and acoustic waveguides of the prior art.

BRIEF DESCRIPTION OF THE DRAWINGS

In the accompanying drawings, in which certain modes of carrying out the present invention are shown for illustrative purposes:

FIG. 1 shows a longitudinal cross section of the invention consisting of the toothbrush handle, an ultrasonic transducer, a plurality of bristle tufts, driving motor, battery, and electronic controls.

FIG. 2 shows the cross section of the brush head displaying the positioning of the ultrasonic transducer between the bristle tufts.

DESCRIPTION OF THE PREFERRED EMBODIMENTS

Figure 3:
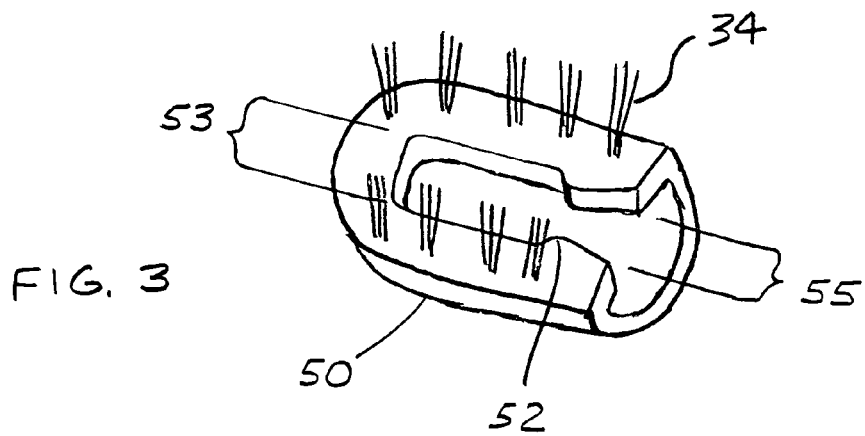
FIG. 3 shows an isometric view of the removable brush head and its locking mechanism.

Description Of The Basic Device.

Referring in detail to the drawings, the reference numerals herein refer to the like numbered parts in the drawings. In the following discussion, unless otherwise qualified, the term "ultrasound" refers to acoustic energy in either continuous wave ultrasound or a repetitive burst type ultrasonic modality, having a frequency higher than 20 kHz. When reference is made to "sonic" or "sonic vibrations", unless otherwise qualified, it is a reference to a vibrating or oscillating motion below 20 kHz frequency. The term "cavitation" in association with the ultrasonic toothbrush refers to the generation, activation, or bursting of bubbles in the fluids in the oral cavity. The reference to "fluids in the oral cavity", unless otherwise qualified, is typically a mixture of saliva, water and dentifrice. "Acoustic streaming" refers to a flow of fluids driven by an acoustic wave emitted by the ultrasonic transducer. When reference is made to "ultrasound transducer" it is a reference to the means of converting electric energy to ultrasonic pressure waves.

The invention of the improved ultrasonic toothbrush 20 in the preferred configuration is shown in FIG. 1 and FIG. 2. The toothbrush 20 comprises of a handle portion 22, a neck portion 23, and a head portion 36 constructed of a rigid plastic material such as Acrylonitrile Butadiene Styrene (ABS), a battery pack 24, an electronic control module 26, an electronic frequency generator module 28, an ultrasound transducer 38, connecting wiring 32, one or more bristle tufts 34, and a driving motor 30.

The best currently available material selection for the ultrasound transducer 38 is typically a PZT-8 piezoelectric ceramic or similar material. The generation of ultrasonic pressure waves by piezoelectric means is a well documented and a well-known science to the people experienced in the ultrasound generating art. The construction of the ultrasound transducer 38 is not limited to piezoelectric ceramics, and not limited to a single element. Numerous other means such as single crystal silicones, capacitive micro-machined ultrasonic transducer materials, and electrostatic polymer foams are available today, and more will be available in the future to construct an ultrasound transducer 38. As it is a common practice of the industry, definition of an ultrasound transducer 38 herein is a transducer comprising one or more elements.

The selection of the ABS material for the toothbrush handle portion 22 and toothbrush head portion 36 is made due to the excellent acoustic characteristic of ABS, and its ability to encapsulate the ultrasound transducer 38. The encapsulation herein also functions as an acoustic matching layer 42 between the front surface 43 of the ultrasound transducer 38 and the fluids in the oral cavity. To increase the efficiency of the ultrasound transducer 38, closed cell foam 40 filler is utilized at the back surface 45 of the ultrasound transducer 38 to redirect the radiation of ultrasonic pressure waves 44 from the back surface 45 of the ultrasound transducer 38 toward the bristle 34 side of the ultrasound transducer 38, thereby significantly increasing the output of the ultrasound transducer 38 toward the oral cavity.

As it is shown in FIG. 2, the ultrasound transducer 38 is ideally positioned between and extends to just below the tips of the bristle tufts 34 to receive and be in intimate contact with the dentifrice applied to the bristle tufts 34 by the user.

Figure 6:
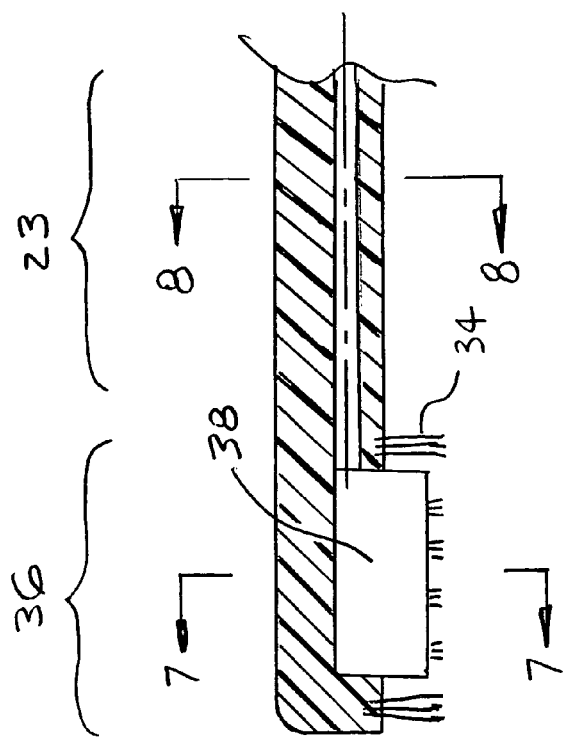
FIG. 6 and FIG. 7 show a simple configuration wherein the ultrasonic transducer is not encapsulated.
Figure 7:
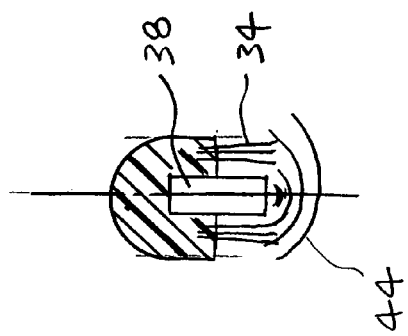

FIG. 6 and FIG. 7 show a simpler construction without encapsulation of the ultrasound transducer 38 and without the application the closed cell foam 40 filler.

Upon activating the toothbrush by the control switch 27 the low voltage DC energy supplied by the battery pack 24 is converted into an ultrasonic frequency DC current by the electronic frequency generator module 28, which is connected to the ultrasound transducer 38 by the connecting wiring 32. Under the influence of the ultrasonic frequency DC current the ultrasound transducer 38 resonates, expands and contracts volumetrically, in tune with the frequency supplied by the electronic frequency generator module 28 and thereby converts the electronic energy into ultrasonic pressure waves 44. These non-attenuated ultrasonic pressure waves 44 are impacting and penetrating teeth and gums and periodontal pockets and creating mild cavitation and acoustic streaming in the fluids within the oral cavity, loosening soft plaque on the surfaces of teeth and gums and in the periodontal pockets formed in the gums around the neck of the teeth. The bristle tufts 34 of the toothbrush 20 then dislodge the loosened soft plaque.

While almost all of the non-attenuated ultrasonic pressure waves 44 are driven directly against the gums and the teeth, some small portion of the pressure waves 44 are transmitted toward the bristles and conducted to the gums and teeth, further increasing the plaque removing capability of the bristle tufts 34.

The time averaged intensity of the ultrasonic pressure waves 44 is ideally limited to approximately 30 mW/cm$^2$, which is effective for the purpose and at the same time it is below the tissue heating range. However, higher intensities can be applied with the appropriate safeguards against tissue heating or damage. The ultrasonic pressure waves 44 could be applied in a continuous wave modality or in a pulsed burse mode modality such as 200-microsecond burse width repeated at 1 kilohertz repetition rate to further limit tissue heating. Depending on the final acoustic energy output of the ultrasound transducer, various burse widths and repetition rates are possible to assure that no tissue damage occurring. The ideal frequency of the ultrasonic pressure waves 44 is between 0.75 MHz and 1.6 MHz, but it can range from 20,000 Hertz to above 2,000,000 Hertz depending on the selection of materials utilized in the toothbrush 20 and the components in the dentifrice to maximize cavitation and acoustic streaming in the fluids of the oral cavity.

The toothbrush handle portion 22 also contains a drive motor 30 and an electronic control module 26. The output shaft of the drive motor 30 typically carries an off-center weight 31. The shaft of the drive motor 30 and the off-center weight 31 attached to it rotate at approximately 9000 rpm, creating a 150 Hertz sonic frequency vibration in the toothbrush 20. The toothbrush 20 is designed with a weight distribution plan wherein the head portion 36 is significantly lighter weight than the loaded weight of the handle portion 22. The neck portion 23 is designed to be lightweight and flexible, to act as a motion transducer. The weight of the handle portion 22 and the user's hand dampens the vibration amplitude of the handle portion 22, while the flexing neck portion 23 causes the head portion 36 to vibrate at a much higher vibration amplitude than the handle portion 22.

Figure 8:
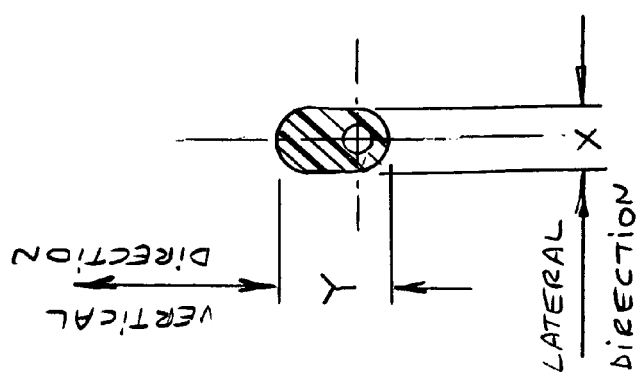
FIG. 8 shows a cross section of the neck portion of the toothbrush, which forms the motion transducer in the motorized design.

The cross section of the neck portion 23 is shown in FIG. 8 to explain the motion transducer function of the neck portion 23. The vibration created by the off center weight 31 and the motor 30 in the handle portion 22 is a circular vibration. A motion transducer by definition converts one form of vibration into another form of vibration. To transform the circular vibration of the handle portion 22 into a lateral vibration of the head portion 36, the dimension Y of the neck portion 23 is selected to be significantly larger than dimension X. Depending on the selection of the ratio between the X and Y the vertical vibration can be practically eliminated while maximizing the lateral vibration.

The electronic control module 26 controls the rotation speed of the drive motor 30. The control switch 27 provides on-off signals to the control module 26 to start the sonic frequency motion of the head portion 36 and the bristle tufts 34. The control switch 27 is also used to send programming impulses to the control module 26 to create higher or lower sonic frequency vibrations of the head portion 36 and the bristle tufts 34 by changing the rotational speeds of the drive motor 30. Lower frequency vibration of the head portion 36 will have smaller vibration amplitude and cause a gentler feedback to the user. Conversely, a higher frequency vibration will have higher vibration amplitude and provide a more powerful feedback to the user. A typical design will provide the user with multiple selectable speed options.

The secondary inductive coil 25 located in the handle portion 22 typically charges the rechargeable battery 24 through the electronic control module 26, which controls the voltage and current to properly charge the battery. The matching primary inductive coil is typically located in a separate charger assembly connected to household current.

The Removable Brush Head.

Figure 4:
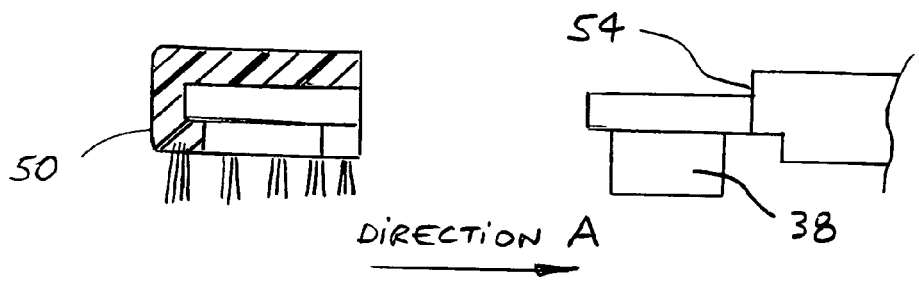
FIG. 4 and FIG. 5 show the removable brush head configuration.
Figure 5:
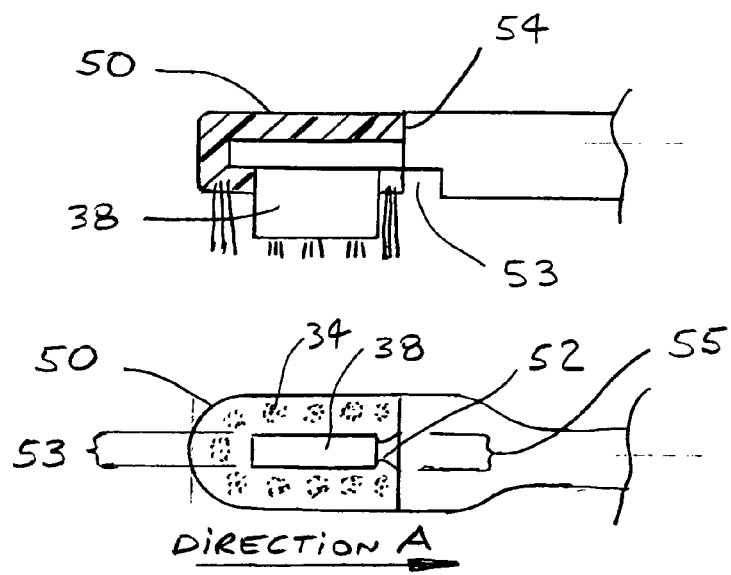

FIG. 3, FIG. 4, and FIG. 5 illustrate the toothbrush with a removable brush head 50 and its installation procedure. Brush head 50 is a tubular construction closed on one end and open on the other end. It is typically molded of a flexible plastic material and designed to be a light press fit onto the tip of the toothbrush handle. The brush head 50 holds at least one bristle tuft 34, but more typically it holds 15 to 30 bristle tufts 34. The bristle tufts 34 are manufactured by the conventional toothbrush technology and typically made of a nylon material. The tips of the bristles are rounded to prevent gum abrasion. The side of the brush head 50 where the bristle tufts 34 are located incorporates a parallel side slot 53 which is slightly wider than the ultrasound transducer 38 and is closed on one end and has a tapered mouth 55 on the open end. The mouth 55 is slightly wider than the slot 53. There are two bumps 52 at the intersection of the parallel side slot 53 and the tapered mouth 55 forming a restriction area. The user positions brush head 50 in front of the tip of the head portion 36 of toothbrush 20 and simply push it onto the tip of head portion 36 in direction A. The tapered mouth 55 slides around the transducer 38 and the restriction formed by the two bumps 52 is forced to open until the restriction clears the end of the ultrasound transducer 38. As the restriction formed by bumps 52 clears the ultrasound transducer 38 it closes into its relaxed size, which locks the brush head 50 into place. The motion of the brush head 50 in the direction A is stopped by shoulder 54. A twisting motion of a coin placed into slot 53 can remove brush head 50.

All referenced patents are hereby incorporated by reference in their entireties.

SCOPE OF THE INVENTION

While the preceding description contain many specificities, these should not be construed as limitations on the scope of the invention, but rather as an exemplification of a preferred embodiment and additional embodiments. Many other variations are possible. A simpler version of the toothbrush can be constructed without encapsulation of the ultrasound transducer, without an impedance matching layer on the ultrasound transducer, and without the closed cell foam filler at the back surface of the ultrasound transducer. The toothbrush may be constructed with a fixed brush head or a removable brush head. The toothbrush may be constructed without a vibrating brush head eliminating the electric motor and the associated motor control, to be less expensive and used as a manual toothbrush with the ultrasonic assist. While a battery charging station is a necessary part of the preferred embodiment utilizing a rechargeable battery, an alternative construction utilizing replaceable batteries instead of the rechargeable batteries eliminates the associated battery charger, which could further reduce the cost of the toothbrush.

Skilled artisans will readily be able to change dimensions, shapes and construction materials of the various components described in the embodiment. Accordingly, the scope of the invention should be determined not by the embodiment illustrated, but by the appended claims and their legal equivalents.

I claim:
1. An ultrasonic toothbrush comprising:
   a) a rigid elongated member of non-conductive material having a handle end and a brush head end;
   b) an ultrasound transducer constructed of at least one element protruding laterally from an upper surface of said brush head end contracting and expanding volumetrically in response to a changing electrical field generating ultrasonic energy and transmitting said ultrasonic energy to the fluid within the oral cavity and to the teeth and gums and periodontal pockets, operative to loosen soft plaque on the surfaces of said teeth and said gums and said periodontal pockets;
   c) means coupled to said ultrasonic transducer operative for generating ultrasonic frequency electronic signals and transmitting said signals to said ultrasonic transducer; and
   d) a removable brush head having at least one bristle tuft protruding from an upper surface thereof, said brush head being substantially hollow so as to be received on the brush head end of the elongated member, said brush head further including a wall portion at the upper surface thereof which includes an elongated slot, a tapered mouth and a restricted area between the elongated slot and the tapered mouth, the tapered mouth adapted to slide around the transducer and the restricted area is adapted to retain the brush head in place when it clears an end of the transducer after which the transducer is located within an extends through the elongated slot of the brush head.

* * * * *